United States Patent [19]
Boswell

[11] Patent Number: 5,226,892
[45] Date of Patent: Jul. 13, 1993

[54] SURGICAL TUBING CLAMP

[76] Inventor: Thomas A. Boswell, 210 Courtney St., Pass Christian, Miss. 39571

[21] Appl. No.: 748,835

[22] Filed: Aug. 23, 1991

[51] Int. Cl.$^5$ ............... A61M 5/32; F16G 15/04; A41F 1/00
[52] U.S. Cl. ............... 604/180; 604/174; 24/543; 24/616; 128/DIG. 26
[58] Field of Search ............ 604/174, 180, 280; 128/128, DIG. 26; 24/116 A, 616, 542, 543

[56] References Cited

U.S. PATENT DOCUMENTS

| | | | |
|---|---|---|---|
| 3,918,446 | 11/1975 | Buttaravoli | 604/180 |
| 4,397,647 | 8/1983 | Gordon | 604/180 |
| 4,457,754 | 7/1984 | Buttaravoli | 604/180 |
| 4,498,903 | 2/1985 | Mathew | 604/174 |
| 4,699,616 | 10/1987 | Nowak et al. | 604/180 |
| 4,754,534 | 7/1988 | Helwick | 24/543 |
| 4,838,878 | 6/1989 | Kalt et al. | 604/180 |
| 4,897,082 | 1/1990 | Erskine | 604/180 |
| 4,897,900 | 2/1990 | Baggett | 24/543 |
| 4,988,338 | 1/1991 | Taylor et al. | 604/180 |
| 5,073,170 | 12/1991 | Schneider | 604/180 |

FOREIGN PATENT DOCUMENTS

| | | | |
|---|---|---|---|
| 2643269 | 8/1990 | France | 604/180 |
| 8001752 | 9/1980 | PCT Int'l Appl. | 24/542 |

Primary Examiner—Michael H. Thaler
Assistant Examiner—Adam J. Cermak
Attorney, Agent, or Firm—Alexander Norcross

[57] ABSTRACT

A clamp for Laprosocopy tubing in surgical procedures. A folded, plastic frame, has a contact adhesive base for non-penetrating affixation to a sterile drape. The foam forms a top and a bottom plate, which are hinged in facing opposition; each contains opposing foam pads for holding, without crimping or crushing, Laprosocopy and other surgical tubing having varying diameters. The plastic frame is sufficiently flexible to form a hinge section, and has a molded-in snap tab closure.

1 Claim, 2 Drawing Sheets

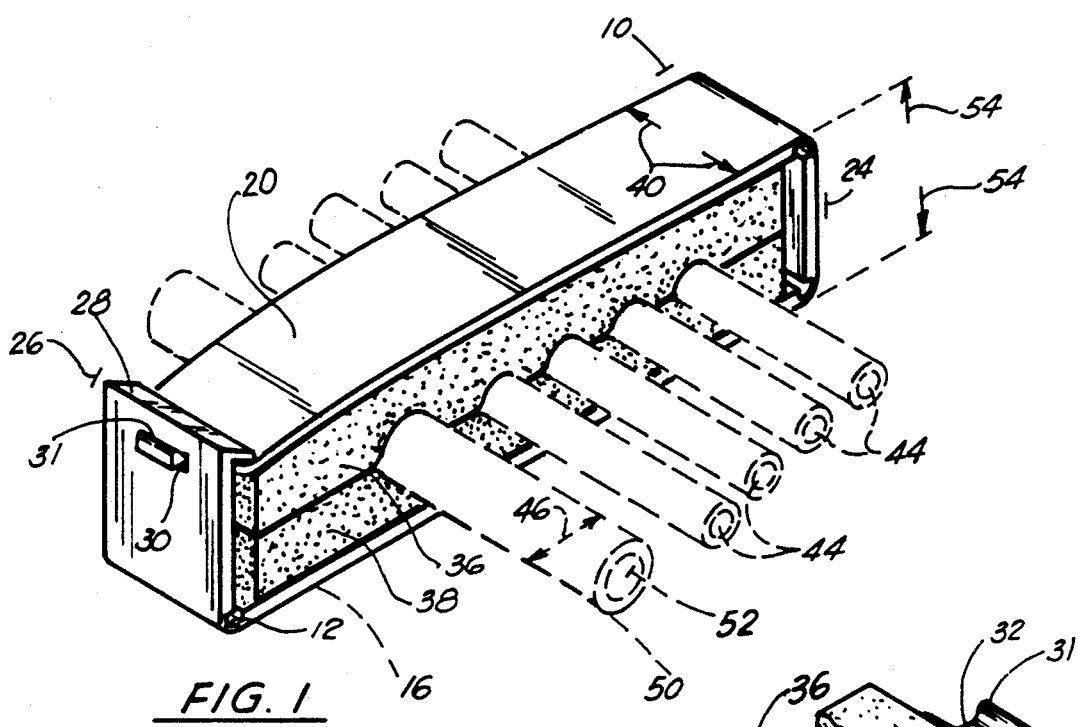
FIG. 1
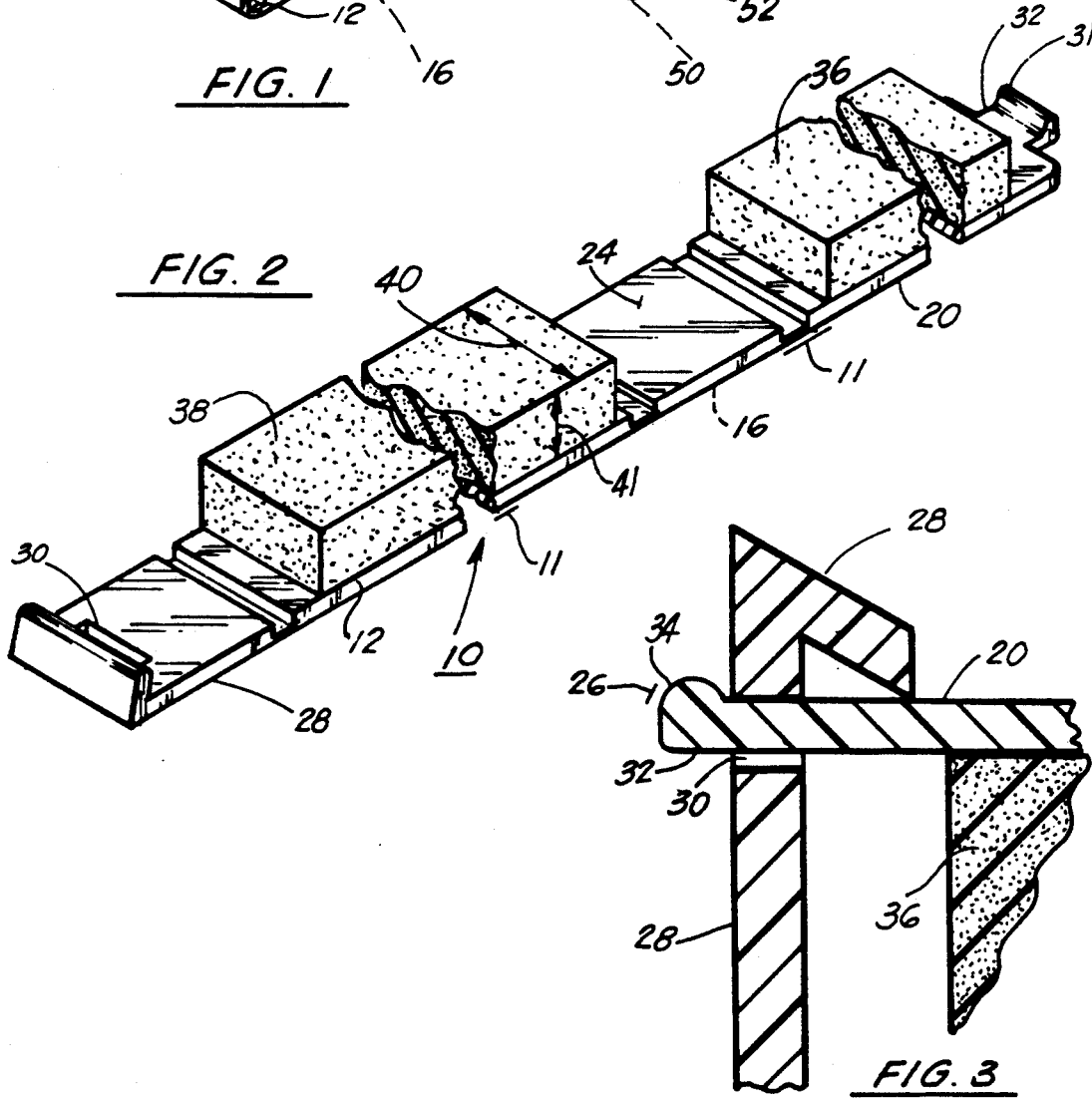
FIG. 2
FIG. 3

SURGICAL TUBING CLAMP

BACKGROUND OF THE INVENTION

This invention relates to the field of securing surgical tubing, especially Laprosocopy tubing, in a sterile field during surgical procedures.

U.S. Pat. No. 4,897,082 to Erskine, for a suture tab, discloses a foldable plastic tab having a fold line or a hinge, and lined with a double-backed adhesive tape. This item is designed to be sutured rather than adhered to a drape or to the skin, for clamping a catheter.

U.S. Pat. No. 4,498,903 to Mathew discloses a tube fixing device for interoral use which comprises a folding plastic clip having a snap over latch, but having fixed diameter, semi-circular recesses for gripping a tube. The item uses a cord, passing between the teeth, to hold the clamp into place. The cord is described as being akin to dental floss.

U.S. Pat. No. 4,397,647 to Gordon discloses a catheter stabilizer. Again, this discloses a plastic unit having a hinged side and a snap over lid, with rigid apertures within the catheter unit for holding a particular size of catheter. This patent does disclose the use of an adhesive base to fasten to the skin of the patient. Also please note that in FIGS. 6 and 7 a differing form or structure of the device is shown, still having a rigid tube opening but a different form of snap over tab.

U.S. Pat. No. 4,726,716 to McGuire discloses a catheter fastening device including an adhesive backing and using Velcro to close the tab over. Note that again, a physical opening is provided for the catheter. This patent differs in also requiring and specifying the opening for the second tube of a Foley catheter. Compare this to the article of No. 13 in the Erskine patent.

U.S. Pat. No. 4,966,590 to Kalt shows a catheter and IV tube holder which comprises a base which is described as being made of, among other things, an expandable foam. The bottom of the base is coated with an allergenic adhesive for adhering to the skin of the patient. A hook and loop fastener material is fastened to the upper side of the base. In turn, a second flexible sheet or flap is provided with a mating hook and loop fastener for clamping of the IV tube between the two sections held together by the hook and loop fastener.

U.S. Pat. No. 4,583,976 to Ferguson discloses a catheter support. The base of the catheter support carries an adhesive compatible for human skin and has a permanently affixed adjoining flap coated with a fastening material which when folded over locks to the tube. FIG. 4 shows the use of a foam material to comprise the base of this clamp, however, the foam is covered with a thin water impermeable shield on the side facing towards the catheter tube.

U.S. Pat. No. 4,170,995 to Levine discloses a fixed catheter clamp having an adhesive base with a screw mechanism rising therefrom and a foldable plastic clamp again having a rigid opening which may be screwed into position. The advantage claimed is that the adjustment of the knot may serve to crimp the catheter tubing to shut off fluid flow.

Only the patents to Erskine, Kalt and Ferguson disclose the use of foam and none of these patents disclose the use of foam pads alone as a frictional gripping, non-crimping clamp for varying sizes of tubing.

SUMMARY OF THE INVENTION

An clamp for a surgical tubing is particularly adapted for securing Laprosocopy tubing, which is a fiber optic tubing which is particularly susceptible to crushing or damage. The invention is an adhesive, clamp retainer for Laprosocopy and other tubing, which may be readily secured to sterile drapes without compromising the sterile field in surgery. It comprises a folded, plastic frame, having a contact adhesive base for non-penetrating affixation to a sterile drape. The frame forms a top and a bottom plate which are hinged in facing opposition; each contains opposing foam pads for holding, without crimping or crushing, Laprosocopy and other surgical tubing having varying diameters. The plastic frame is sufficiently flexible to form a hinge section, and has a molded-in snap tab closure.

A particular advantage of this form of clamp is that it is incapable of damaging relatively delicate fiber optic tubing, by clamping positively, but without imposing a crushing or bending force on the tubing. The tubing is secured by a conformable, high friction grip that exerts minimal crushing forces, but is capable of securing tubing of varying sizes against lateral motion or withdrawal.

It is thus an object of this invention to disclose a surgical tubing clamp which secures tubing of varying sizes against lateral motion.

It is a further object of this invention to disclose a surgical tubing clamp which secures tubing against lateral motion without crushing delicate or fragile tubing.

It is a further object of this invention to disclose a surgical tubing clamp which secures Laprosocopy tubing against lateral motion without crushing or excessive clamping forces.

It is a further object of this invention to disclose a surgical tubing clamp which secures Laporosocopy tubing against lateral motion without compromising the sterile field in surgery.

It is a further object of this invention to disclose a surgical tubing clamp which secures Laprosocopy tubing against lateral motion without crushing or excessive clamping forces, yet also securely clamps other surgical tubing of varying sizes.

This and other objects of the invention can be seen more clearly from the detailed description of the preferred embodiment which follows.

BRIEF DESCRIPTION OF THE DRAWINGS

FIG. 1 is an angled view of the clamp in closed position.

FIG. 2 is a view of the open clamp, showing the hinging.

FIG. 3 is a detail view of the latch of the clamp.

DETAILED DESCRIPTION OF THE PREFERRED EMBODIMENT

Figure 4:
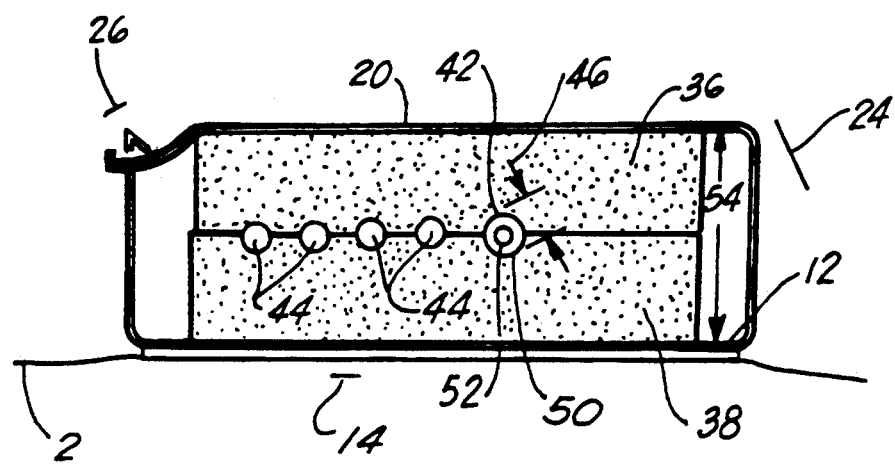
FIG. 4 is a side view of the clamp in closed position.

An understanding of the inventive clamp 10 requires an understanding of the particular problem presented by such surgical tubing as Laproscopy tubing 42. Such tubing has become far more sophisticated than the classic hollow flexible plastic tube used to convey fluids from or to the patient's body. Surgical tubing now is used to introduce sensors into the body, and to convey light, vision and electrical signals. Laprosocopy tubing 42, as one example, is a fiber optic tube for viewing the interior of the body; as such it comprises an outer sheath 50 over an optical grade glass fiber optic bundle 52. The sheath 50 must be made flexible to permit the Laprosocopy tubing 42 to be bent and inserted into the body of the patient; the fiber optic bundle 52 is extremely delicate and susceptible to damage, especially by crimping or crushing of the Laprosocopy tubing 42.

All such surgical tubing is inserted, one end into a patient, and affixed at its other end to various machines and apparatus within the operating area. As a result some means must be provided for clamping the tubing to prevent inadvertent displacement of the inserted end due to accidental movement of the attached equipment. Such a clamp must not compromise the sterile field by penetrating or tearing the drapes; the clamp itself must be preferably disposable to decrease contamination problems. Of greatest importance, the clamp must secure the tubing without damaging the tubing.

I show in FIG. 1 a side view of the inventive clamp 10. In its preferred embodiment, the clamp 10 is constructed from a single continuous strip 11 of flexible plastic. this strip 11 is folded to form in sequence, a top plate 20, a hinge 24, a base plate 12, and means 22 for holding the top plate 20 and base plate 12 in opposed juxtaposition.

The preferred form of such means for holding the two plates in opposed juxtaposition to one another is the formation of a hinge 24 in the plastic strip by folding the strip, so that the top plate 20 and base plate 12 are a spaced distance 54 apart, yet the strip 11 is so folded over that the top plate 20 is in opposed juxtaposition to the bottom plate 12 when the clamp 10 is closed. The clamp 10 is then held in this position by a latch 26.

In the preferred embodiment, latch 26 may be formed of the continuous strip 11 by forming a closing lip 28 at one end of the strip 11, and providing a rectangular hole 30 in the lip 28; an engaging tab, sixed to insert in the hole 30, is formed at the other end of the strip 11. A snap protrusion 34 is formed at the end of the engaging tab 32 so that, when the tab 32 is inserted into the hole 30, the natural spring forces of the strip 11 will push the tab 32 to one side of the hole 30, latching the tab 32 to the closing lip 28, forming a snap latch 26 which may be readily opened, yet will remain securely closed.

It should be clear to those of skill in the art that other forms of snap latch may be molded or formed as part of the continuous strip 11. In addition, a much wider range of means for holding the top plate 20 and base plate 12 may be used, including formed or separate hinges and latches, or various interlocked tabs, such as Velcro strips. However, since sterility considerations make it beneficial that the clamp 10 be disposable, the low cost and ready producibility make the embodiment described preferred.

Since the clamp must hold surgical tubing 44 against motion, some means 14 for affixing the clamp relative to the patient must be provided. It is important that the sterile field not be compromised. This requires that the clamp cannot be affixed to the patient's skin (or the clamp 10 would have to be sterilized and the skin prepped). It is preferred that the means 14 for affixing the clamp 10 fix the clamp to the sterile surgical drapes 2 which block off and mask the sterile operating field; the drapes 2 may not be penetrated, and thus the clamp cannot be sewn, stapled or pinned to the drapes.

The preferred embodiment therefore provides, as the means 14 for affixing the clamp 10, an adhesive strip 16 running substantially the entire length of the base plate. This adhesive may be any of the commonly available contact adhesives suitable for affixing plastic to cloth or paper. The adhesive is sealed against accidental contact by a masking paper backing.

Affixed to both the top plate 20 and the base plate 12, are two opposed flexible pads for enclosing the tubing 42,44 with sufficient contact to frictionally restrain the tubing 42,44 from lateral movement, yet with a minimal non-crushing force. This non-crushing restraint is provided by providing the pad as an upper foam pad 36, affixed to the top plate 20, and a lower foam pad 38 affixed to the base plate 12. Each of the upper pad 36 and the lower pad 38 are made of a thickness 41 which is several times the maximum diameter 46 of the clamped tubing 42,44. The combined pad thickness 41 is slightly greater than the spaced distance 54 of the opposed top and base plates in the closed clamp 10, producing a positive closing pressure by the pads 36,38 on the clamped tubing. Nevertheless, since the pads are thicker than the maximum diameter of any enclosed tubing, the foam deforms uniformly around the tubing and no crushing forces are produced.

An advantage of this construction is that no provision need be made for any particular size of tubing; in the prior art notched clamps, by contrast, each clamp notch had to be exactly sized to the tubing outer diameter, and specific clamps had therefore to be provided for each different tube. One size of the inventive clamp 10, by contrast, will serve for a wide range of tubing sizes.

The Clamp 10 does not secure the tubing 42,44 by gripping force, but rather by the cumulative effect of friction by the foam pad on the tubing 42,44. For this reason, the opposed pads 36,38 should be of a sufficient width to provide such friction without pulling out. In practice, in a typical clamp having a top plate about $3\frac{1}{2}$ inches long, a pad width of $\frac{3}{4}$ inch is sufficient to secure the tubing.

In operation, the clamp is positioned on the surgical drapes adjacent the run to the surgical Laprosocopy tubing 42 and other tubing 44. The backing paper 18 is removed, and the clamp 10 affixed to the drapes 2 in the chosen position by the contact adhesive strip 16. The tubing is placed on the lower foam pad 38, and the top plate 20 closed over the base plate 12, folding the clamp around the hinge 24, and latching the clamp 10 closed with the snap latch 26. This closes the upper pad 36 against the lower pad 38 around the tubing 42,44. The thickness of the pads 36,38 insures that no crushing forces are imposed on the tubing, yet the positive closure, occasioned by the thickness 41 of the pads being greater than the closed distance 54 of the top plate 20 and base plate 12, insures sufficient frictional retention of the tubing to adequately secure the tubing against unwanted motion.

The construction of the clamp 10, being of a single formed plastic strip 11 with attached foam pads 36,38 and adhesive strip 16, is particularly suited to inexpensive mass production. The clamp may be readily sterilized by gas or radiation sterilization for one time use, and then disposed of after use, all at less cost than required for a reuseable clamp with repeated sterilizations.

It can thus be seen that the invention is of particular value both for its safe clamping of delicate surgical tubing, for its more universal application to clamp a variety of tubing, and for its low cost. the invention has been described in one preferred low cost form, but extends beyond the one embodiment to those wider equivalents as are inherent in the claims.

I claim:

1. A non-crushing tubing clamp comprising:

a base plate;

means for affixing said base plate to a surface of a surgical drape, securely, and without penetration thereof;

a top plate;

means for latching said top plate a spaced distance apart from, and in opposing juxtaposition to said base plate;

a first deformable, frictional non-adhesive pad on said top plate and a second deformable, frictional non-adhesive pad on said base plate, said first and said second pad being in opposed facing relationship when said top plate is in opposing juxtaposition to said base plate;

said first and said second pads being, together, thicker than said spaced distance;

wherein said means for affixing comprises an adhesive strip for affixing said base plate to said drape.

* * * * *